United States Patent [19]
Frelinger et al.

[11] Patent Number: 6,100,444
[45] Date of Patent: *Aug. 8, 2000

[54] PROSTATE SPECIFIC REGULATORY NUCLEIC ACID SEQUENCES AND TRANSGENIC NON-HUMAN ANIMALS EXPRESSING PROSTATE SPECIFIC ANTIGEN

[75] Inventors: John G. Frelinger, Pittsford; Richard K. Barth, Rochester; Chungwen Wei, Pittsford, all of N.Y.

[73] Assignee: University of Rochester Medical Center, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/797,722

[22] Filed: Feb. 11, 1997

[51] Int. Cl.$^7$ ................................ C12N 5/00; C12N 5/10; C12N 5/18; C07H 21/04

[52] U.S. Cl. .................................. 800/18; 800/21; 800/23; 800/25; 435/325; 435/354; 435/320.1; 536/23.1; 536/23.5; 536/24.1

[58] Field of Search ............................... 435/240.2, 240.4, 435/320.1; 536/24.1, 23.1, 23.5; 800/9, 10, 13, 21, 23, 25, 18; 935/325, 354

[56] References Cited

U.S. PATENT DOCUMENTS

| | | | |
|---|---|---|---|
| 5,416,017 | 5/1995 | Burton et al. | 435/240.2 |
| 5,648,478 | 7/1997 | Henderson | 536/241 |

FOREIGN PATENT DOCUMENTS

WO 95/19434   7/1995   WIPO .

OTHER PUBLICATIONS

Lundwall A. (Biochem. Biophys. Res. Commu. vol. 161 (3) 1989, 1151–1159).
Grisolano et. al. (Proc. Natl. Aca. Sci. Sep. 1994, vol. 91 (19) 8989–93). Abstract only.
Lee et al. (Anticancer Res. Aug. 7, 1996, 16:1805–1812).
Wagner et al. Genetic Engineering: Principles and Methods. 1988, vol. 10, p221–246, (p. 221 and p. 238 Only).
Houdebine L.–M. J. Biotechnol. 34, 1994, 269–287.
Wall R. J. Theriogenology, 45, 57–68, 1996.
Augee, M. L. Platypus and Echidnas. The Royal Zoological Society of New South Wales, New South Wales. 1992, Section of Reproduction.
Hew et al. US 5,545,808, 1996, Aug. (First page and Column 4 only).
Wight et al. Transgenic mice: a decade of progress in technology and research. Mutation Research, vol. 307, pp. 429–440, Jun. 1, 1994.
Gordon et al., "Regulation of Thy–1 Gene Expression in Transgenic Mice", *Cell,* vol. 50, 445–452, Jul. 31, 1987.
Eades–Perner et al., "Mice Transgenic for the Human Carcinoembyronic Antigen Gene Maintain Its Spatiotemporal Expression Pattern", *Cancer Research,* 54, 4169–4176, Aug. 1, 1994.
Schaffner et al., "Transgenic Mice Carrying A PSArasT24 Hybrid Gene Develop Salivary Gland and Gastrointestinal Tract Neoplasms", *Laboratory Investigation,* vol. 72, No. 3, p. 283, 1995.
Greenberg et al., "Prostate cancer in a transgenic mouse", *Proc. Natl. Acad. Sci.,* vol. 92, pp. 3439–3443, Apr. 1995.
Wei et al., "Expression of human prostate–specific antigen (PSA) in a mouse tumor cell line reduces tumorigenicity and elicits PSA–specific cytotoxic T lymphocytes", *Cancer Immunol. Immunother,* (1996) 42:362–368.
Schuur et al., "Prostate–specific Antigen Expression Is Regulated by an Upstream Enhancer", *The Journal of Biological Chemistry,* vol. 271, No. 12, pp. 7043–7051, Mar. 22, 1996.
Frelinger et al., "Targeted CTL–mediated immunity for prostate cancer: development of human PSA–expressing transgenic mice", AACR Meeting, Apr. 20–24, 1996 (Abstract).
Frelinger et al., "Targeted CTL–Mediated Immunity for Prostate Cancer: Development of Human PSA–Expressing Transgenic Mice", 1st Annual Meeting of the Pepper Centers, May 13–15, 1996 (Abstract).
Wei et al., "Development of human PSA–expressing transgenic mice to investigate targeted CTL–mediated immunity for prostate cancer", ASBMB/ASIP/AAI Joint Meeting, Jun. 2–6, 1996 (Abstract).
Frelinger et al., "Targeted CTL–Mediated Immunity for Prostate Cancer: Development of Human PSA–Expressing Transgenic Mice", First International Conference of Immunology and Aging, Jun. 16–19, 1996 (Abstract).
Cleutjens et al., Journ. Biolog. Chem., 271:6379–6388 (1996).
Cleutjens et al., Mol. Endocrinol., 11:148–161 (1997).
Lundwall et al., FEBS, 214:317–322 (1987).
Riegman et al., Biochem. & Biophys. Res. Com., 159:95–102 (1989).
Riegman et al., FEBS, 247:123–126 (1989).
Riegman et al., Mol. Endocrinol., 5:1921–1930 (1991).
Shulz et al., Nucl. Acids Res., 16:6226 (1988).

*Primary Examiner*—Deborah J. Clark
*Attorney, Agent, or Firm*—Fish & Richardson P.C.

[57] ABSTRACT

The non-coding regulatory sequences of the prostate specific antigen (PSA) are described. Non-human transgenic animals are also provided which express human PSA, which is non-naturally occurring in non-human animals.

16 Claims, 4 Drawing Sheets

PROSTATE SPECIFIC REGULATORY NUCLEIC ACID SEQUENCES AND TRANSGENIC NON-HUMAN ANIMALS EXPRESSING PROSTATE SPECIFIC ANTIGEN

The present invention was made with support under grant numbers CA11198, POAG 104643 and CA70218 awarded by the National Institutes of Health. The government has certain rights in this invention.

BACKGROUND OF THE INVENTION

1. Field of the Invention

This invention relates generally to transgenic non-human animals which express a gene not naturally occurring in the animal. More specifically, the invention relates to transgenic non-human animals which express human prostate specific antigen.

2. Description of Related Art

Prostate cancer is the second leading cause of cancer deaths in American men. Although this disease is rarely seen in men under the age of 50, the incidence of prostate cancer increases rapidly in subsequent decades of life. Surgery, radiation and hormonal therapies are the standard treatments for prostate cancer, however, these conventional therapies ultimately are ineffective for metastatic disease. Immunotherapy mediated through cytotoxic T lymphocytes (CTL) offers a promising treatment avenue, since T cells, in principle, can migrate throughout the body and specifically recognize and destroy metastatic tumor cells in an antigen specific manner.

Prostate cancer cells express a well characterized antigen, prostate-specific antigen (PSA), whose expression is widely used clinically as a marker for prostate cancer. PSA, a kallikrein with serine protease activity, has a highly restricted tissue distribution and is expressed in the normal epithelial cells of the prostate gland, the same cell type from which most prostate tumors arise. Neither the regulation of PSA expression nor the role of PSA in normal or neoplastic prostate cells is well understood.

An obvious concern in using PSA as a target antigen for immunotherapy is that it is a self-antigen. To date, much of the work on tumor immunotherapy has implicitly assumed that it is necessary to identify and characterize antigens that are specifically and uniquely expressed in tumors but not in normal tissues. However, this assumption may not be warranted. For example, recent work has revealed that many targets for anti-melanoma CTL, such as tyrosinase, MART-1, gp100 and gp75, are normal self-antigens specific to the melanocyte lineage (V. Brichard et al., *J. Exp. Med.* 178:489–495, 1993; A. B. Bakker et al., *J. Exp. Med.* 179:1005–1009, 1994; S. L. Topalian et al., *Proc. Natl. Aca. Sci USA* 91:3515–3519, 1994; R. F. Wang et al., *J. Exp. Med.* 181:799–804, 1995). Further, the existence of a number of tissue-specific autoimmune diseases supports the concept that self-reactive immune effectors can be activated under appropriate conditions. Taken together, these findings raise the possibility that tissue-specific differentiation antigens could serve as targets for immunotherapy for other cancers besides melanoma. Thus, it may not be necessary to first isolate anti-tumor CTL from patients in order to identify the target antigens for characterization. Instead, it may be possible to induce a cell-mediated immune response against a normal tissue-specific antigen whether or not such responses typically occur in patients.

The study of PSA as a potential target antigen for immunotherapy, as well as other studies investigating its physiologic role, has been hampered by the lack of appropriate animal models. There is no currently available mouse system to model the salient immunological aspects of prostate cancer, as no prostate-specific kallikrein has been reported for mice.

SUMMARY OF THE INVENTION

The present invention is based on the discovery of the regulatory region of the human PSA gene and the production a transgenic non-human animal that expresses the human PSA gene. Using a 14 kb genomic DNA region which encompasses the entire human PSA gene and adjacent flanking sequences, a series of human PSA transgenic mice were generated. In the six independent lines of transgenic mice, the expression of the human PSA transgene, driven by its own cis-acting regulatory elements, was specifically targeted to the prostate. Tissue distribution analysis demonstrated that PSA transgene expression was similar to the human expression pattern. Immunohistochemical analysis of the prostate tissue also showed that the expression of the PSA transgene was confined to the ductal epithelial cells. Despite expressing PSA as a self-antigen in the prostate, these transgenic mice were able to mount a cytotoxic immune response against PSA expressed by tumor cells, indicating that expression of the transgene had not resulted in complete nonresponsiveness.

In a first embodiment, the present invention provides a nucleic acid construct containing a non-coding regulatory sequence isolated from a human prostate specific antigen gene. The non-coding regulatory sequence is operably associated with a nucleic acid sequence which expresses a product, such as a protein of interest or an antisense RNA, for example. The nucleic acid sequence is heterologous to the non-coding sequence. The non-coding regulatory sequence of the present invention is the human prostate specific antigen promoter and/or enhancer region, which allows tissue-specific expression in the prostate.

In another embodiment, the prostate specific antigen regulatory sequence is used to provide increased transcription of a nucleic acid sequence, specifically in the prostate of an animal. Such nucleic acid sequences include therapeutic genes such as thymidine kinase as a suicide gene or other genes such as those encoding growth factors or growth factor receptors which could be involved in prostate cancer or in the development of benign prostatic hyperplasia (BPH).

In yet another embodiment, the invention provides transgenic non-human animals characterized as expressing human prostate specific antigen, which is non-naturally occurring in the animal.

Figure 1:
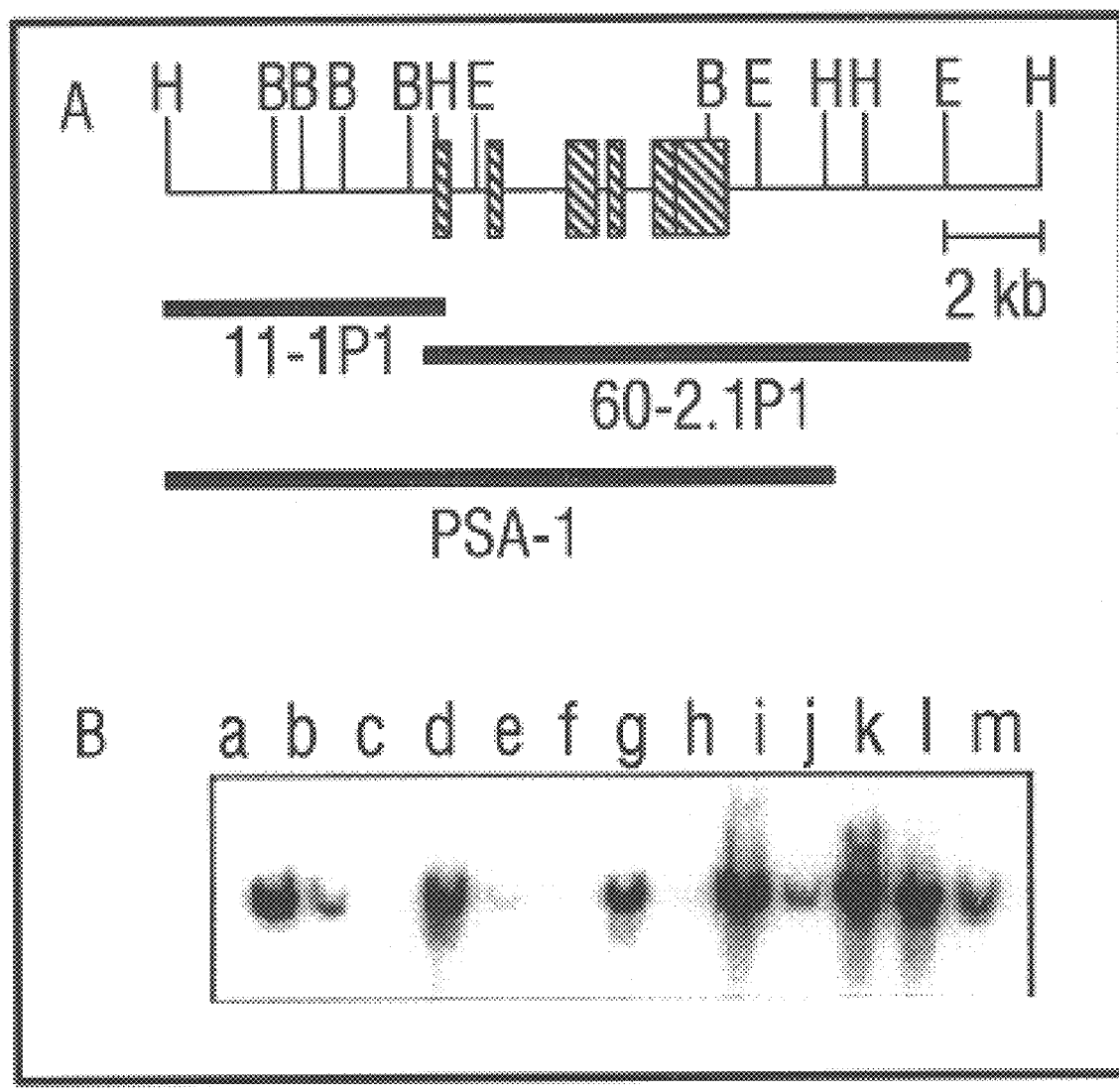
FIG. 1A is a schematic diagram of the PSA-1 transgene construct. The lambda clones, 60-2.1P1 and 11-1P1, and the assembled PSA-1 transgene construct are depicted in relation to the genomic map. Solid boxes indicate exons, and open box indicates 3' untranslated region of the PSA gene. The 5' untranslated region is not included because of its small size.
FIG. 1B shows a Southern blot of genomic DNA from mouse tails used to analyze the incorporation of the PSA-1 transgene construct into the mouse genome. Lanes a to c show normal mouse DNA with an additional equivalent of 10, 1 and 0 copies of the pBS/PSA-1 plasmid per diploid genome to serve as copy number controls; lanes d to l show 9 independent PSA1 transgenic founders designated as P1-1 through P1-9, respectively; lane m shows human hepatoma G2 DNA as a positive control.
Figure 1C:
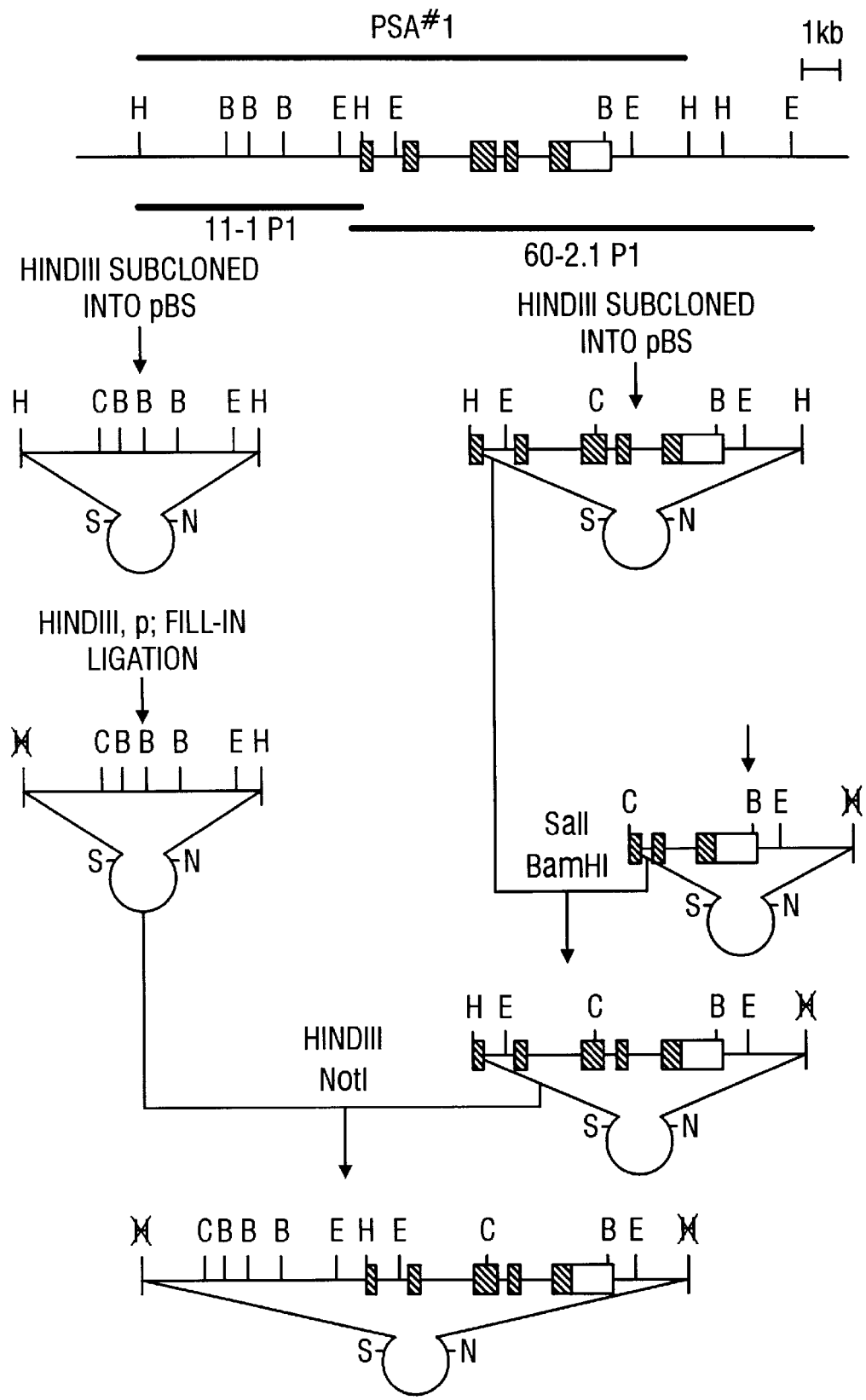

FIG. 1C shows a restriction map of PSA structural gene and regulatory regions.

FIGS. 2A, 2B and 2C show RT-PCR analysis of the expression of PSA transgene in the prostate of the PSA1 transgenics. PSA PCR products were visualized by either ethidium bromide staining (A), or Southern blotting using an internal fragment as the probe (B), and b-actin PCR products by ethidium bromide staining (C). Lane a, non-transgenic; b, P1-2; c, P1-4; d, P1-6; e, P1-7; f, P1-8; g, P1-9; h, LNCaP.

FIGS. 3A–D show analyses of the tissue distribution of PSA mRNA in the PSA1 transgenics by Northern blotting. Five μg of the total RNA isolated from various tissues of a male P1-6 (A), a male P1-8 (B), a male P1-9 (C), and a female P1-9 (D) transgenic mice were resolved on 1% formaldehyde-agarose gels, transferred to nylon membranes, then hybridized with the labeled PSA cDNA probe. These tissues were: lane a, prostate; b, testis; c, coagulating glands/seminal vesicle; d, spleen; e, kidney; f, liver; g, thymus, h, heart, i, lung; j, salivary glands; k, brain; l, ovary; m, uterus; and n, 5 μg of LNCaP total RNA in each blot to serve as an internal control.

FIGS. 4A–D show the localization of PSA expression in the prostate of the PSA1 transgenics by immunohistochemical staining. Formalin-fixed, paraffin-embedded tissue sections from the prostate of a P1 -9 transgenic (A, B) and a nontransgenic control (C, D) were incubated with rabbit anti-human PSA (A, C) or control rabbit immunoglobulin (B, D), followed by HRP-conjugated goat anti-rabbit Ig, and then visualized by adding diaminobenzidine as the chromogen.

FIGS. 5A–D show graphs illustrating the cytotoxic activity of TIL from line 1/PSA tumors. Nontransgenic (A, C), and transgenic mice (B, D) were injected in the hind flank i.m. with $2 \times 10^4$ line 1/PSA cells. Tumors were allowed to grow for 20 days, and TIL were isolated and used as effector cells in a 6-hr $^{51}$Cr-release assay. Targets were line 1 (squares) and line 1/PSA (circles) induced to express class I with dimethyl sulfoxide.

DETAILED DESCRIPTION OF THE INVENTION

The present invention allows production of non-human transgenic animals that express human prostate specific antigen. This exemplary animal model provides a system for identifying factors associated with non-responsiveness to PSA. Such factors allow the development of immunotherapy regimes for human prostate cancer using PSA as the target antigen. Identification of the PSA regulatory elements also allows construction of specific gene therapy vectors for targeting to the prostate. For example, the prostate-specific regulatory sequences can be used in conjunction with "suicide" genes or other therapeutic genes to treat diseases of the prostate.

The PSA gene regulatory sequence is located in the non-coding region of the gene and exhibits strong expression in prostate tissue. Approximately 6 kilobases (kb) of 5' non-coding sequence and 2 kb of 3' non-coding sequence was isolated upstream and downstream, respectively, from the coding sequence, as described in the Examples herein. FIG. 1C shows a restriction map of the PSA gene, including coding and non-coding regions. Since the PSA coding region is also included in the construct, the regulatory region may also include non-coding intron sequences. The transcription regulatory sequences include transcriptional control regions such as TATAA and CAAT box sequences as well as sequences which regulate the tissue specificity of the transcribed product. In the nucleic acid construct of the invention, the ATG start codon is typically provided by the nucleic acid sequence expressing the product of interest.

As used herein, the term "regulatory sequence" or "regulatory element" refers to a nucleic acid sequence capable of controlling the transcription of an operably associated gene. A regulatory sequence of the invention may include a promoter, an enhancer and/or a silencer, for example. Therefore, placing a gene under the regulatory control of a promoter or a regulatory element means positioning the gene such that the expression of the gene is controlled by the regulatory sequence(s). In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates. Enhancers are believed to be relatively position and orientation independent in contrast to promoter elements. The noncoding sequences or intron sequences (e.g., which contain regulatory sequences) which are used in the invention construct are not more than about 9 kbp in length.

One may identify a convenient restriction site in the 5' untranslated region of the PSA gene at the ends of the nucleic acid sequence of interest. Alternatively, an adaptor which will join the nucleic acid sequence of interest to the PSA gene may be used. Another strategy which may employed is to introduce a multiple cloning site into the 5'-untranslated region of the PSA gene for the purpose of inserting the nucleic acid sequence of interest.

As an alternative strategy, a plasmid as exemplified in FIG. 1C, which has a unique HindIII site for insertion of a nucleic acid sequence of interest, can be designed. This allows prostate tissue-specific expression of the inserted cDNA or genomic clone. Further modifications of the vector include the addition of a polylinker at the unique HindIII site.

Regulatory sequence function during expression of a gene under its regulatory control and can be tested at the transcriptional stage using DNA/RNA and RNA/RNA hybridization assays (e.g., in situ hybridization, nucleic acid hybridization in solution or solid support) and at the translational stage using specific functional assays for the protein synthesized (e.g., by enzymatic activity, by immunoassay of the protein, by in vitro translation of mRNA or expression in microinjected xenopus oocytes).

As used herein, the term "nucleic acid sequence" refers to a polymer of deoxy-ribonucleotides or ribonucleotides, in the form of a separate fragment or as a component of a larger construct. Nucleic acids expressing the products of interest can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences.

Nucleic acid sequences utilized in the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). Sequences for specific genes can also be found in GenBank, National Institutes of Health computer database.

The phrase "nucleic acid sequence expressing a product of interest" refers to a structural gene which expresses a biologically active protein of interest or an antisense RNA for example. The term "structural gene" excludes the non-coding regulatory sequence which drives transcription. The structural gene may be derived in whole or in part from any source known to the art, including a plant, a fungus, an animal, a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions. The structural gene may also encode a fusion protein. It is contemplated that introduction into animal tissue of nucleic acid constructs of the invention will include constructions wherein the structural gene and its regulatory sequence e.g., PSA regulatory sequence, are each derived from different animal species.

The term "heterologous nucleic acid sequence" as used herein refers to at least one structural gene which is operably associated with the regulatory sequence of the invention. The nucleic acid sequence originates in a foreign species, or, in the same species if substantially modified from its original form. For example, the term "heterologous nucleic acid sequence" includes a nucleic acid originating in the same species, where such sequence is operably linked to a regulatory sequence that differs from the natural or wild-type regulatory sequence (e.g., PSA regulatory sequence).

The term "operably associated" refers to functional linkage between the regulatory sequence and the structural gene regulated by the regulatory sequence. The operably linked regulatory sequence controls the expression of the product expressed by the structural gene. Alternatively, the functional linkage also includes an enhancer element.

"Promoter" means the minimal nucleotide sequence sufficient to direct transcription. Also included in the invention are those promoter elements that are sufficient to render promoter-dependent gene expression controllable for cell-type specific, tissue specific, or inducible by external signals or agents; such elements may be located in the 5' or 3' regions of the native gene, or in the introns.

"Gene expression" means the process by which a nucleotide sequence undergoes successful transcription and translation such that detectable levels of the delivered nucleotide sequence are expressed in an amount and over a time period so that a functional biological effect is achieved. "Expressible genetic construct" as used herein means a construct which has the PSA regulatory sequences positioned with a nucleic acid encoding a desired product, such that the nucleic acid is expressed.

Examples of genes encoding therapeutic agents which can be used in the invention construct, for example for immunotherapy, include genes encoding toxins. The nucleic acid sequence encoding a protein of interest in the invention construct includes immuno-modulators and other biological response modifiers. The term "biological response modifiers" encompasses substances which are involved in modifying the immune response in such manner as to enhance the destruction of tumor, for example. Examples of immune response modifiers include such compounds as lymphokines. Lymphokines include tumor necrosis factor, the interleukins, lymphotoxin, macrophage activating factor, migration inhibition factor, colony stimulating factor, and interferon. Included in this category are immunopotentiating agents including nucleic acids encoding a number of the cytokines classified as "interleukins". These include, for example, interleukins 1 through 12. Also included in this category, although not necessarily working according to the same mechanisms, are interferons, and in particular gamma interferon (γ-IFN), tumor necrosis factor (TNF) and granulocyte-macrophage-colony stimulating factor (GM-CSF). Nucleic acids encoding growth factors, toxic peptides, ligands, receptors, suicide factors (e.g., TK) or other physiologically important proteins can also be introduced into specific cells of the prostate.

Sense or antisense nucleic acids can also be used in the invention construct. For example, a sense polynucleotide sequence (the DNA coding strand) encoding a polypeptide can be introduced into the cell to increase expression of a "normal" gene. Other cell disorders can also be treated with nucleic acid sequences that interfere with expression at the translational level. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme. Alternatively, the method includes administration of a reagent that mimics the action or effect of a gene product or blocks the action of the gene. Therefore, when a prostate tumor is etiologically linked with over expression of a polynucleotide, it would be desirable to administer an inhibiting reagent such as an antisense polynucleotide.

The use of antisense methods to inhibit the in vitro translation of genes is well known in the art (see, e.g., Marcus-Sakura, *Anal. Biochem.*, 172:289, 1988). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (see, e.g., Weintraub, *Scientific American*, 262:40, 1990). The antisense nucleic acids hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10–12 nucleotides in length, for example, at least 15, 20, 25, 50, 75, or 100 nucleotides in length. The antisense nucleic acid can also be as long as the target nucleic acid with which it is intended to form an inhibitory duplex. As is described further below, the antisense nucleic acids can be introduced into cells as antisense oligonucleotides, or can be produced in a cell in which a nucleic acid encoding the antisense nucleic acid has been introduced by, for example, using gene therapy methods.

The present invention also provides gene therapy for the treatment of a tumor or disease which is in the prostate. Such therapy would achieve its therapeutic effect by introduction of the appropriate polynucleotide which contains a therapeutic gene for example, into cells of subjects having the disorder. Delivery of invention constructs can be achieved using a recombinant expression vector such as a chimeric virus or a colloidal dispersion system.

Gene therapy methods as described herein can be performed in vivo or ex vivo. In addition, it may be preferable to remove the majority of a tumor prior to gene therapy, for example surgically or by radiation.

Various viral vectors which can be utilized for gene therapy as taught herein include adenovirus, herpes virus, vaccinia, or, preferably, an RNA virus such as a retrovirus. Preferably, the retro viral vector is a derivative of a murine or avian retro virus. Examples of retro viral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retro viral vectors can incorporate multiple genes. All of these vectors can transfer or incorporate a gene for a selectable marker so that transduced cells can be identified and generated. By inserting a sequence (including promoter region) of interest into the viral vector, along with another gene which encodes the ligand for a receptor on a specific target cell, for example, the vector is now target specific. Preferred targeting is accomplished by using an antibody to target the retro viral vector. Those of skill in the art will know of, or can readily ascertain without undue experimentation, specific polynucleotide sequences which can be inserted into the retro viral genome, for example, to allow target specific delivery of the retro viral vector containing the polynucleotide.

Since recombinant retro viruses are defective, they require assistance in order to produce infectious vector particles. This assistance can be provided, for example, by using helper cell lines that contain plasmids encoding all of the structural genes of the retro virus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\psi$2, PA317 and PA12, for example. These cell lines produce empty virions, since no genome is packaged. If a retro viral vector is introduced into such cells in which the packaging signal is intact, but the structural genes are replaced by other genes of interest, the vector can be packaged and vector virion produced.

Another targeted delivery system for the invention construct is a colloidal dispersion system. Colloidal dispersion systems include macromolecule complexes, nano-capsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

In another embodiment, the present invention provides a transgenic non-human animal that expresses human prostate specific antigen. Using a 14 kb genomic DNA region which encompasses the entire human PSA gene and adjacent flanking sequences, a series of human PSA transgenic mice were generated as the exemplary model animals. In the six independent lines of transgenic mice generated, the expression of the human PSA transgene, driven by its own cis-acting regulatory elements, is specifically targeted to the prostate. Tissue distribution analysis demonstrated that PSA transgene expression closely follows the human expression pattern. Immunohistochemical analysis of the prostate tissue also showed that the expression of the PSA transgene is confined to the ductal epithelial cells. Despite expressing PSA as a self-antigen in the prostate, these transgenic mice were able to mount a cytotoxic immune response against PSA expressed by tumor cells, indicating that expression of the transgene has not resulted in complete nonresponsiveness.

The "non-human animals" of the invention comprise any non-human animal having a prostate. Such non-human animals include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Retroviral infection can also be used to introduce transgene into a non-human animal. The developing non-human embryo can be cultured in vitro to the blastocyst stage. During this time, the blastomeres can be targets for retro viral infection (Jaenich, R., *Proc. Natl. Acad. Sci USA* 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode human prostate specific antigen which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The above disclosure generally describes the present invention. A more complete understanding can be obtained by reference to the following specific examples which are provided herein for purposes of illustration only and are not intended to limit the scope of the invention.

EXAMPLE 1

Generation of PSA-1 Construct and Transgenic Mice

In brief, a PSA cDNA clone described previously (C. Wei et al., *Cancer Immunol. Immunother.* 42:362–368, 1996) was used to screen a human lymph node genomic library (ATCC, Rockville, Md., 20852 USA, Accession No. ATCC 57760). A lambda clone encompassing the PSA gene was isolated (clone 60-2.1P1)(FIGS. 1a and 1c). The 5' end of this clone was then used as a probe to screen a human chromosome 19-specific genomic library (ATCC 57711) to isolate clone 11-1P1 (FIGS. 1a and 1c). These lambda clones were engineered by standard recombinant DNA techniques into pBluescript vector, resulting in a plasmid clone called pBS/PSA-1.

After removing the vector sequence, the PSA-1 transgene construct was microinjected into fertilized embryos from the intercross of (C57BL/6J X DBA/2J) $F_1$ hybrid mice as described (Dragone et al., *Proc. Natl. Aca. Sci USA* 92:626–630, 1995). Transgenic founders, collectively called PSA1 transgenics, were backcrossed to BALB/cByJ mice (H-$2^d$) to established transgenic lines semi-syngeneic to the PSA-expressing line 1 cells (H-$2^d$) used in the TIL experiments described below. Line 1 is a small cell lung carcinoma cell line derived from a female BALB/c mouse (J. M. Yuhas, *Cancer Res.* 34: 722–728, 1974). Line 1/PSA, a PSA-expressing line 1 transfectant, was generated and characterized previously (C. Wei, supra). LNCaP, a human prostatic cell line, was obtained from the American Type Culture Collection (CRL 1740).

Transgenic mice were generated using the PSA-1 transgene construct which covers 14 kb of genomic sequence. It contains approximately 6 kb of 5' flanking sequence and 2 kb of 3' flanking sequence, in addition to the PSA coding region. Therefore, the PSA regulatory region may also include non-coding intron sequences. FIG. 1A is a schematic diagram of the PSA-1 transgene construct. The lambda clones, 60-2.1P1 and 11-1P1, and the assembled PSA-1 transgene construct are depicted in relation to the genomic map. Solid boxes indicate exons, and open box indicates 3' untranslated region of the PSA gene. The 5' untranslated region is not included because of its small size.

Of the 94 offspring generated and screened, nine founders were identified which had incorporated the transgene. FIG. 1B shows a Southern blot of genomic DNA from mouse tails used to analyze the incorporation of the PSA-1 transgene construct into the mouse genome. Extracted DNA was digested with Bam HI, resolved on a 0.7% agarose gel, transferred to a nylon membrane, and probed with labeled PSA cDNA. (lanes a to c) normal mouse DNA with an additional equivalent of 10, 1 and 0 copies of the pBS/PSA-1 plasmid per diploid genome to serve as copy number controls; (lanes d to l) 9 independent PSA1 transgenic founders designated as P1-1 through P1-9, respectively; lane m is human hepatoma G2 DNA to serve as a positive control.

Of the nine founders, six were able to transmit the transgene through their germline and the transgenic lines P1-2, P1-4, P1-6, P1-7, P1-8 and P1-9 were established. The transgenic lines varied in the number of copies of the transgene they had incorporated, as determined by comparing transgenic bands to copy number controls of plasmid. High copy-number transgenic lines (approximately 10 copies per diploid genome) included lines P1-4, P1-6, P1-8 and P1-9, whereas P1-2 and P1-7 were low copy-number lines (approximately 1 copy per diploid genome).

EXAMPLE 2

Expression of Human PSA in the Prostate of Transgenic Mice

Southern blot analysis to identify mice which have incorporated the transgene and Northern blot analysis to analyze the tissue distribution of the transgene expression were performed as described (J. Sambrook, *Molecular Cloning A Laboratory Manual* (Cold Spring Harbor Lab. Press, Plainview, N.Y.) 1989). In both cases, the probe used was the full-length PSA cDNA labeled by the random hexamer method. For RT-PCR analysis, total RNA isolated from various tissues was reverse transcribed and subjected to PCR amplification using the following intron-spanning primer sets with the indicated numbers of cycle: PSA PCR primer set (5'CTTGTGGCCTCTCG3', SEQ ID NO:1 and 5'GAGGGTGAACTTGC3', SEQ ID NO:2; 35 cycles), mouse b-actin PCR primer set (5'ATGGATGACGATATCGCTG3', SEQ ID NO:3 and 5'ATGAGGTAGTCTGTCAGGT3', SEQ ID NO:4; 25 cycles) and human b-actin PCR primer set (5'GTGGGGCGCCCCAGGCACCA3', SEQ ID NO:5 and 5'CTCCTTAATGTCACGCACGATTTC3', SEQ ID NO:6; 25 cycles). PSA RT-PCR products were further analyzed by Southern blotting using an internal fragment (nt158 to nt524) as the probe, which was also labeled by the random hexamer method.

Figure 2:
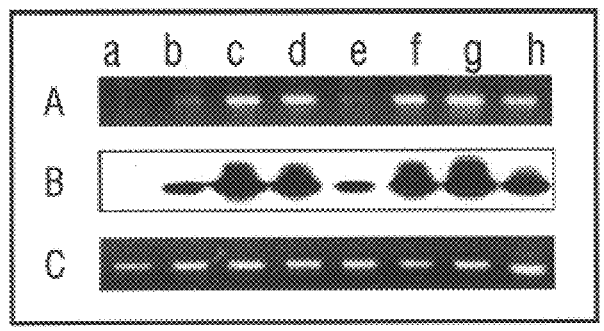

RT-PCR analysis was performed to examine the expression of human PSA transgene in the prostate of the transgenic mice. Total RNA, isolated from mouse prostate and the human prostatic cell line LNCaP, was reverse transcribed into cDNA, which was then subjected to PCR amplification using PSA-specific primers. FIG. 2 shows Northern blots analyzing the expression of PSA transgene in the prostate of the PSA1 transgenics. Total RNA was isolated from the prostate of the nontransgenic and six PSA1 transgenic lines and the human prostatic cell line LNCaP, and RT-PCR was performed with PSA-specific primers, mouse and human b-actin primers. PSA PCR products were visualized by either ethidium bromide staining (A), or Southern blotting using an internal fragment as the probe (B), and b-actin PCR products by ethidium bromide staining (C). Lane a, nontransgenic; b, P1-2; c, P1-4; d, P1-6; e, P1-7; f, P1-8; g, P1-9; h, LNCaP.

As shown in FIG. 2A, prostate RNA from all the transgenic lines, as well as RNA from LNCaP, resulted in bands by ethidium bromide staining; whereas prostate RNA from the nontransgenic control did not, indicating that the PSA PCR primers do not cross-react with any mouse gene product. To further ensure that the amplified bands corresponded to PSA, they were probed with a fragment of PSA cDNA which is internal to the RT-PCR product. All the transgenic lines showed hybridization to the internal fragment (FIG. 2B), demonstrating that human PSA mRNA is expressed in the prostate of all the six independent PSA1 transgenic lines. RT-PCR was also performed using mouse and human b-actin primer sets to ensure the integrity of the isolated mouse prostate RNA and LNCaP RNA, respectively (FIG. 2C).

Figure 3:
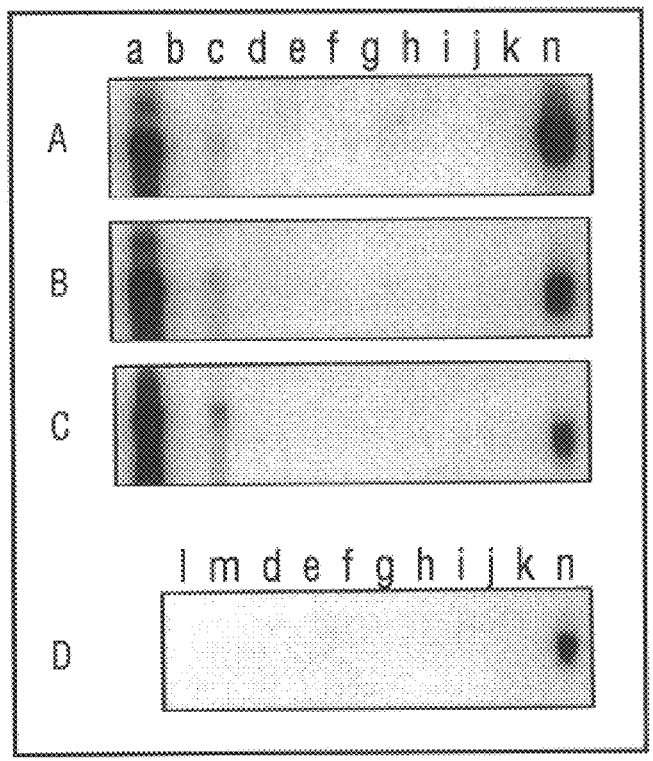

To examine the tissue expression of PSA mRNA, Northern blot analysis was performed on a panel of tissues isolated from males of a nontransgenic control and three independent transgenic lines (P1-6, P1-8 and P1-9). FIG. 3 shows an analysis of the tissue distribution of PSA mRNA in the PSA1 transgenics by Northern blotting. Five $\mu$g of the total RNA isolated from various tissues of a male P1-6 (A), a male P1-8 (B), a male P1-9 (C), and a female P1-9 (D) transgenic mouse were resolved on 1% formaldehyde-agarose gels, transferred to nylon membranes, then hybridized with the labeled PSA cDNA probe. These tissues were: lane a, prostate; b, testis; c, coagulating glands/seminal vesicle; d, spleen; e, kidney; f, liver; g, thymus, h, heart, i, lung; j, salivary glands; k, brain; l, ovary; m, uterus; and n, 5 mg of LNCaP total RNA in each blot to serve as an internal control. Areas between 1 and 2 kb of the blots are shown, hence, only the 1.5 kb major transcript and the 1.9 kb minor alternatively spliced product are visible.

The PSA cDNA probe did not cross-react with any of the mouse kallikrein gene products, as none of the tissues from the nontransgenic control hybridized to the probe. In contrast, an intense band of 1.5 kb, corresponding to the major transcript of human PSA mRNA (D. M. Peehl et al., *Cancer* 75 (Suppl), 2021–2026 1995; P. H. Riegman et al., *Biochem. Biophys. Res. Commun.* 155: 181–188, 1988), was evident in the prostate of the three PSA1 transgenic lines analyzed and in LNCaP (FIGS. 3A to C). By normalizing to the hybridization intensity of the PSA mRNA in LNCaP, the expression levels of the PSA transgene in P1-6, P1-8 and P1-9 were 0.65-, 1.45- and 1.65-fold of the level seen in LNCaP, respectively. Furthermore, like LNCaP and two other human prostate tumor lines (PC 82 and PC EW) (P. H. Riegman et al., supra), four minor alternatively spliced transcripts with the sizes of 5.6, 4.7, 3.2 and 1.9 kb were also observed for the transgene in the prostate of these transgenic mice. This indicates that the PSA transgene not only is expressed in the prostate of the transgenics, but also processed the same way as in humans. The lower molecular weight products, seen in the prostate RNA blot, may represent alternative splicing as well as partial degradation of the RNA.

Even though the Northern blots were intentionally overexposed, the PSA transgene message was not detectable in testis, spleen, kidney, liver, thymus, heart, lung, salivary glands and brain in any of the three transgenic lines analyzed (FIGS. 3A to C). Significantly, salivary glands and kidney, which are known to express high levels of mouse kallikreins (B. H. Van Leeuwen et al., *J. Biol. Chem* 261: 5529–5535, 1986; J. A. Clements et al., *Endocr. Rev.* 10: 339–419, 1989), were negative for transgene expression. In addition, the thymus, a critical tissue in the induction of immue tolerance, was also negative. Serial dilution analysis of the LNCaP RNA showed that the Northern blot analysis could detect as little as 0.5% of the PSA expression level seen in LNCaP. Since levels of PSA mRNA in the prostate of these transgenics were comparable to that of the LNCaP, if PSA is expressed in any of the non-prostate tissues, their levels must be less than 0.5% of that detected in the prostate. Of interest was the weak, but detectable expression in the RNA isolated from coagulating glands/seminal vesicle tissue. Based on developmental and anatomical studies, the coagulating glands in rodents are thought to be analogous to the middle lobe of the human prostate (D. Price et al., *Natl. Cancer Inst. Monogr.* 12: 1–27, 1963). Hence, expression of human PSA transgene in this tissue would be expected if the transgenic mice were to mimic the human expression pattern. Further Northern blot analysis was also performed on a panel of tissues isolated from a female of the P1-9 transgenic line. No transgene expression was observed in any tissues of the female transgenic mouse, including ovary and uterus (FIG. 3D). These data show that the human PSA transgene is specifically expressed in the prostate tissue but is not expressed detectably in most other tissues. The highly restricted tissue distribution of the PSA transgene is strikingly similar to the PSA expression pattern reported for humans (D. M. Peehl et al., supra), 2021–2026, 1995; J. A. Clements et al., *Mol. Cell. Endocrinol.* 99:C1–C6, 1994). Further, male mice as described in FIG. 3 were found to express PSA in serum at approximately the same levels as human males (2–5 ng/ml).

Figure 4:
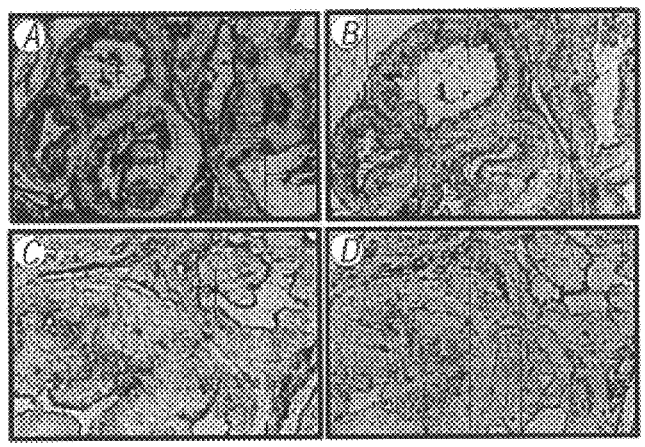

The expression of PSA in the prostate gland was examined by immunocytochemical analysis. Immunohistochemistry using a specific rabbit anti-human PSA antibody demonstrated expression of PSA in the ductal epithelial cells, with the presence of secretory material in the lumen of the glands from the transgenic mice (FIG. 4A). FIGS. 4A–D show the localization of PSA expression in the prostate of the PSA1 transgenics by immunohistochemical staining. Formalin-fixed, paraffin-embedded tissue sections from the prostate of a P1-9 transgenic (panels A, B) and a nontransgenic control (panels C, D) were incubated with rabbit anti-human PSA (panels A, C) or control rabbit immunoglobulin (panels B, D), followed by HRP-conjugated goat anti-rabbit Ig, and then visualized by adding diaminobenzidine as the chromogen.

Control sections, in which the primary rabbit anti-PSA antibody was replaced with normal rabbit immunoglobulin, showed little staining (FIG. 4B). This pattern was essentially identical to the staining we had observed on human prostate sections using these reagents. Prostate tissue from nontransgenic mice exhibited no staining above background (FIGS. 4C and D). Thus, these results demonstrate that the PSA protein is present in the epithelial cells of the prostate in the transgenic mice, in a manner strikingly reminiscent of the human pattern of expression.

EXAMPLE 3

Transgenic Mice Mount a CTL Response to PSA

To determine if the PSA transgenic mice were capable of mounting an immune response to PSA expressed by a tumor, transgenic (line P1-9) and nontransgenic mice were injected with $2 \times 10^4$ line 1/PSA cells i.m. in the rear flank. Prostate tissues removed from nontransgenic or transgenic mice were fixed in formalin, embedded with parafin, and sections (5 $\mu$m) were placed onto poly-L-lysine-coated slides. Following quenching of endogenous peroxidase, the sections were blocked with normal goat serum, stained with a 1:200 dilution of rabbit anti-human PSA (Dako) followed by goat anti-rabbit Ig conjugated to horse radish peroxidase (Dako), and visualized by adding metal-enhanced DAB (Pierce) as the substrate.

Tumor-infiltrating lymphocytes (TIL) were purified from tumors grown in transgenic or nontransgenic mice 20 days after injection of $2 \times 10^4$ line 1/PSA cells using paramagnetic beads (Dynal) conjugated with anti-Thy-1 monoclonal antibody, as described previously (A. J. McAdam et al., *J. Immunother* 15: 155–164, 1994). TIL from tumor-bearing mice were assayed for cytotoxic activity in a standard six-hour assay, against $^{51}$Cr-labeled target cells (2000/well) at various effector-to-target ratios, as previously described (J. L. Maryanski et al., *Eur. J. Immunol* 12: 401–406, 1982).

Figure 5:
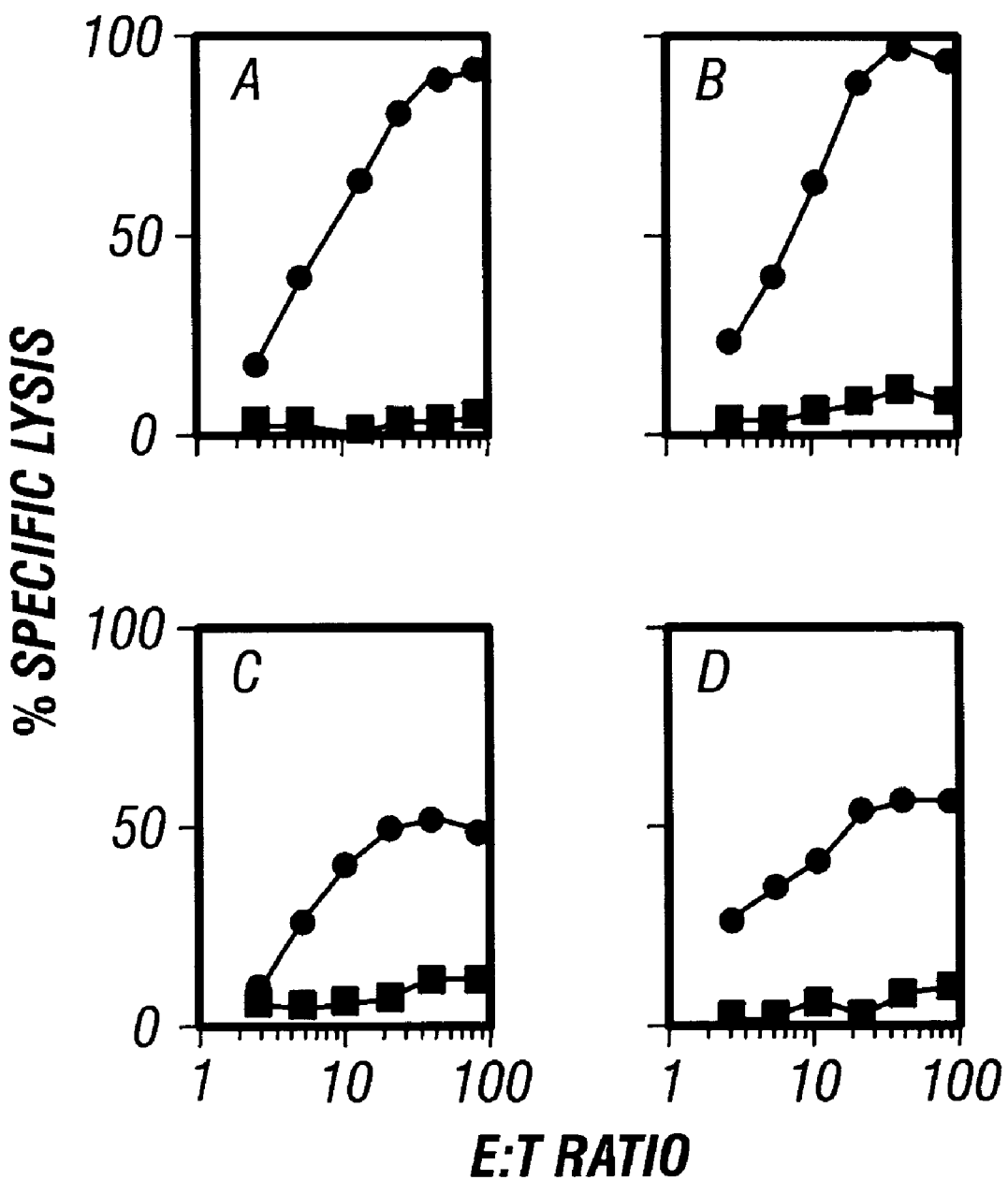

To determine if the PSA transgenic mice were capable of mounting an immune response to PSA expressed by a tumor, transgenic (line P1-9) and nontransgenic mice were injected with $2 \times 10^4$ line 1/PSA cells i.m. in the rear flank. Twenty days later, mice were sacrificed and the tumors removed. TIL were isolated from the tumors and the ability of these primary CTL to lyse parental line 1 or line 1/PSA tumor cells was evaluated in a six-hour $^{51}$Cr-release assay. Results of two such experiments are illustrated in FIG. 5. FIGS. 5 A–D show graphs illustrating the cytotoxic activity of TIL from line 1/PSA tumors. Nontransgenic (A, C), and transgenic mice (B, D) were injected in the hind flank i.m. with $2 \times 10^4$ line 1/PSA cells. Tumors were allowed to grow for 20 days, and TIL were isolated and used as effector cells in a 6-hr $^{51}$Cr-release assay. Targets were line 1 (squares) and line 1/PSA (circles) induced to express class I with dimethyl sulfoxide as described previously (D. W. Bahler et al., *J. Immunol.* 134: 2790–2798, 1985).

The nontransgenic mice were able to mount a vigorous response specific for the PSA antigen, as the PSA-expressing tumor cells were lysed to a high level while the control parental line 1 cells were not lysed (FIGS. 5A, C). The transgenic female mice, being negative for transgene expression, also showed a high level of PSA-specific lysis as expected (data not shown). Remarkably, despite the expression of PSA as a self-antigen in the prostate of the transgenic male mice, they also responded specifically to the PSA-expressing tumor cells (FIGS. 5B, D). Although the CTL response appears similar between transgenic and nontransgenic mice, further analysis at the clonal level will be necessary to determine if the responses in the transgenic and nontransgenic mice are indeed identical. Nevertheless, it appears that these transgenic mice are able to mount a PSA-specific cytolytic response, indicating that expression of the transgene in the prostate has not resulted in complete nonresponsiveness.

Although the invention has been described with reference to the presently preferred embodiment, it should be understood that various modifications can be made without departing from the spirit of the invention. Accordingly, the invention is limited only by the following claims.

What is claimed is:

1. An isolated nucleic acid sequence comprising a 5' non-coding regulatory sequence about 6 kb in length of human prostate specific antigen gene and a 3' non-coding regulatory sequence of human prostate specific antigen gene.

2. The nucleic acid sequence of claim 1, wherein said 3' non-coding regulatory sequence comprises a sequence about 2 kb in length.

3. The nucleic acid sequence of claim 1, further comprising an intron of human prostate specific antigen gene.

4. A nucleic acid construct, comprising a heterologous nucleic acid sequence operatively linked to the nucleic acid sequence of claim 1.

5. The nucleic acid construct of claim 4, further comprising a transcriptional and translational initiation region and a transcriptional termination region functional in an animal cell.

6. The nucleic acid construct of claim 4, wherein the heterologous nucleic acid sequence encodes an agent selected from the group consisting of an immunomodulator, a biological response modifier, an antisense nucleic acid, and a ribozyme.

7. The nucleic acid construct of claim 4, wherein the heterologous nucleic acid sequence encodes a biologically active protein.

8. The nucleic acid construct of claim 4, wherein the heterologous nucleic acid sequence contains an antisense RNA for regulating expression of an endogenous coding sequence.

9. An isolated prostate cell or coagulating gland/seminal vesicle cell, wherein said cell is isolated from a transgenic mouse comprising a nucleic acid construct according to claim 4.

10. A non-human transformed cell comprising the nucleic acid construct of claim 4, wherein said cell expresses said heterologous sequence.

11. An isolated transformed cell comprising the nucleic acid construct of claim 4, wherein said cell expresses said heterologous sequence.

12. A transgenic mouse, comprising a nucleic acid construct according to claim 4, wherein the heterologous nucleic acid sequence is expressed in prostate tissue at detectable levels.

13. A transgenic mouse that expresses human prostate specific antigen in prostate tissue, said human prostate specific antigen otherwise not naturally occurring in said mouse, said expression being conferred by a transgene contained in the somatic and germ cells of said mouse, said transgene comprising a nucleic acid sequence which encodes a human prostate specific antigen polypeptide operably linked to a human prostate specific antigen non-coding regulatory sequence, wherein said expression of human prostate specific antigen in said prostate tissue is at detectable levels in said mouse.

14. A method for producing a transgenic mouse that expresses detectable levels of human prostate specific antigen in prostate tissue, human prostate specific antigen otherwise not naturally occurring in said mouse, said method comprising:

a) introducing a transgene into an embryo of a mouse, said transgene comprising a DNA construct encoding a human prostate specific antigen operably linked to a human prostate specific antigen non-coding regulatory sequence, b) transplanting said embryo into a pseudopregnant animal, c) allowing said embryo to develop to term, and d) identifying at least one transgenic offspring containing said transgene that expresses human prostate specific antigen at detectable levels in prostate tissue.

15. The method of claim 14, wherein said introducing of said transgene into said embryo is by introducing an embryonic stem cell containing said transgene into said embryo.

16. The method of claim 14, wherein said introducing of said transgene into said embryo is by infecting said embryo with a retrovirus containing said transgene.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:1:

CTTGTGGCCT CTCG                                                        14

(2) INFORMATION FOR SEQ ID NO:2:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:2:

GAGGGTGAAC TTGC                                                        14

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:3:

ATGGATGACG ATATCGCTG                                                   19

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:4:

ATGAGGTAGT CTGTCAGGT                                                   19

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

GTGGGGCGCC CCAGGCACCA                                                  20

(2) INFORMATION FOR SEQ ID NO:6:

(i) SEQUENCE CHARACTERISTICS:
        (A) LENGTH: 24 base pairs
        (B) TYPE: nucleic acid

```
            (C) STRANDEDNESS: single
            (D) TOPOLOGY: linear (xi) SEQUENCE DESCRIPTION: SEQ ID NO:6:

CTCCTTAATG TCACGCACGA TTTC                                               24
```